United States Patent [19]

Peterson

[11] Patent Number: 4,639,980

[45] Date of Patent: Feb. 3, 1987

[54] TUBING ORGANIZER

[75] Inventor: Drew Peterson, Golita, Calif.

[73] Assignee: Hall Surgical, Division of Zimmer, Inc., Carpinteria, Calif.

[21] Appl. No.: 614,032

[22] Filed: May 25, 1984

[51] Int. Cl.⁴ ............................................. A44B 21/00
[52] U.S. Cl. ............................... 24/306; 128/DIG. 14; 128/DIG. 26; 24/302
[58] Field of Search ................... 24/306, 334; 128/133, 128/384, 385, DIG. 26, DIG. 15, DIG. 19; 248/68.1, 74.3

[56] References Cited

U.S. PATENT DOCUMENTS

| | | | |
|---|---|---|---|
| 2,035,717 | 3/1936 | Pentz | 24/302 |
| 2,896,889 | 7/1959 | Hershberger et al. | 24/302 X |
| 2,943,623 | 7/1960 | Thompson | 128/DIG. 14 |
| 2,969,216 | 1/1961 | Hallsey | 24/302 X |
| 3,387,345 | 6/1968 | Savoir | 24/446 |
| 3,726,280 | 4/1973 | Lacount | 128/DIG. 26 X |
| 3,835,505 | 9/1974 | Shewbridge | 24/302 X |
| 4,047,651 | 9/1977 | McMullen | 24/306 X |
| 4,308,642 | 1/1982 | Heyman | 24/306 |

OTHER PUBLICATIONS

Plastic World, Expanded PTFE—It's a Whole New Ball Game, Jul. 1971.
Journal of Teflon, 1971.

Primary Examiner—William E. Lyddane
Assistant Examiner—Peter A. Aschenbrenner
Attorney, Agent, or Firm—Robert D. Yeager; Christine R. Ethridge

[57] ABSTRACT

An improved tubing organizer for hospital use having Velcro ® straps, a Teflon ® loop and a stainless steel clip connected by stainless steel eyelets. The improved tubing organizer is able to withstand repeated exposure to temperatures up to two hundred eighty degrees Fahrenheit and can be permanently attached to a length of tubing.

4 Claims, 3 Drawing Figures

TUBING ORGANIZER

BACKGROUND OF THE INVENTION

1. Field of the Invention

The present invention relates to devices for holding and organizing tubing, more particularly to devices designed for hospital use to hold tubing in a secure manner.

2. Description of the Prior Art

During the course of hospitalization patients often require the use of support equipment to aid in their recovery. The tubing which connects the patient to the equipment, such as oxygen, anesthesia, intravenous fluids or monitoring equipment, can create a hazard for the patient and hospital personnel if allowed to dangle freely across the floor. In the interest of safety, various devices have been developed to organize the tubing and fasten it to another object such as the bed frame, sheets or drapery.

One such device manufactured under the name Dale Hug ® by Baka Manufacturing Company, Inc., uses two Velcro ® strips stitched together at one end. A Mylar ® strip which is stitched to the opposite end of one of the strips connects the strips to a stainless steel clip. One or more tubes can be pressed between the Velcro ® strips and fastened to the bedsheets or drapery with the clip to hold the tubing safely. A similar device is disclosed in U.S. Pat. No. 4,308,642.

In order to be used repeatedly, the organizing devices must be sterilized before being transferred from one patient to another. A recurrent problem with conventional tubing organizers is the rapid deterioration due to repeated exposure to the high temperatures of sterilization equipment.

Furthermore, the organizers cannot be permanently attached to a particular length of tubing due to the ease with which the Velcro ® strips can be pulled apart. Permanent attachment of the organizers to certain heavily utilized equipment would save time for busy hospital personnel and increase the likelihood that the organizers will be used regularly.

Accordingly, there is a need for a tubing organizer for hospital use which will withstand repeated exposure to high temperatures, thus increasing the useful life span of the devices. There is a further need for such an organizer which can be permanently attached to a length of tubing.

SUMMARY OF THE INVENTION

The present invention is a device for fastening and organizing one or more tubes to an object. The device is an improvement over conventional tube organizers. The device includes a first strap which has a surface of fine, densely matted fibers, a second strap which is so secured at one end to the first strap that it has a surface opposing the matted surface of the first strap. The opposing surface has a plurality of generally rigid barbed extensions which are adapted to adhere to the matted fibers of the matted surface when the two surfaces are pressed together. The device also includes a loop, which is preferably a third strap folded over on itself to form a loop, means, preferably a stainless steel clip, to attach the first strap to an object, and means, preferably stainless steel eyelets, to secure the loop, the attaching means and the second strap to the first strap.

The materials which are used to make the improved device are capable of withstanding exposure to temperatures up to two hundred eighty degrees Fahrenheit. The first and second straps are flexible, high-temperature nylon Velcro ® strips. The preferred arrangement of the improved device would place the loop, preferably made of Teflon ®, between one end of the first strap and the clip. The second strap would be placed on the opposite end of the first strap. A first stainless steel eyelet should hold the clip, loop and first strap together and a second stainless steel eyelet should secure the second strap to the first strap. A third eyelet may be used to hold the first strap to the loop, thus maintaining alignment of the loop along the first strap.

BRIEF DESCRIPTION OF THE DRAWINGS

The following detailed description of the preferred embodiment can be better understood if reference is made to the attached drawings in which.

DETAILED DESCRIPTION OF THE PREFERRED EMBODIMENT

Figure 1:
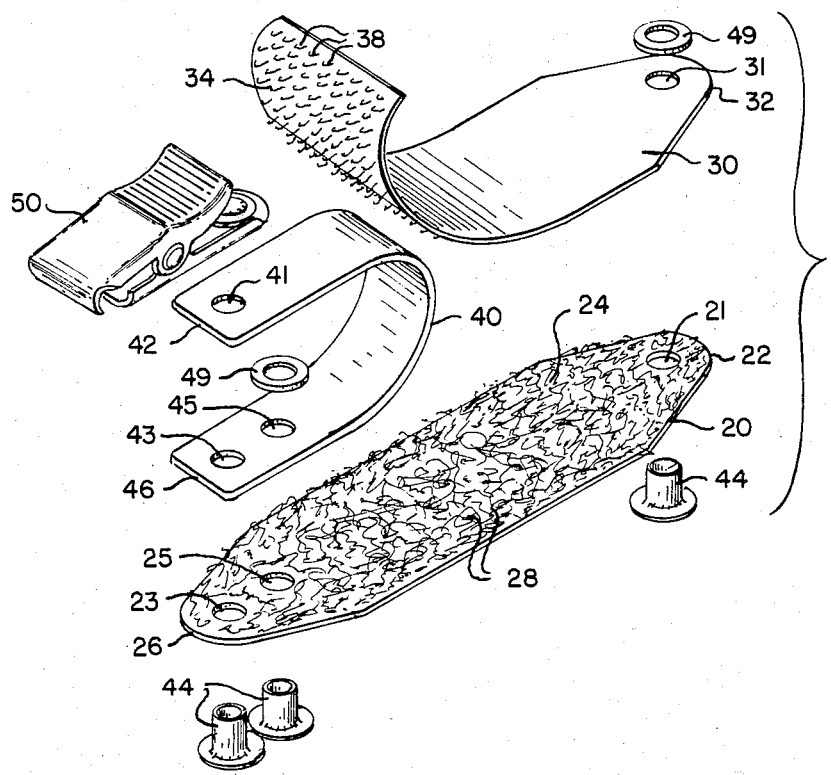
FIG. 1 is an exploded view of the parts of the invention.
Figure 2:
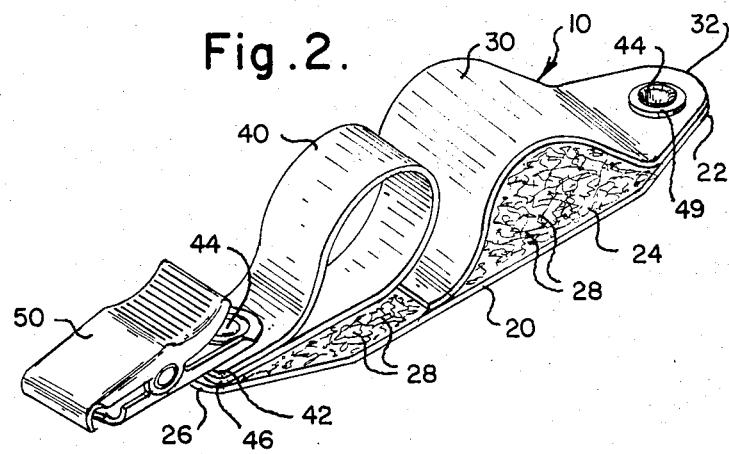
FIG. 2 is a perspective view of the invention.
Figure 3:
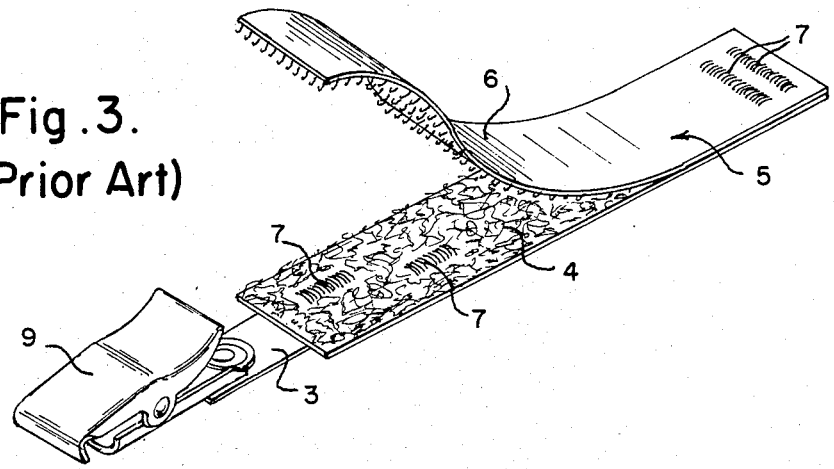
FIG. 3 is a perspective view of the prior art device over which the present invention is an improvement.

The present invention, as illustrated in FIGS. 1 and 2, is a tubing organizer which improves upon the prior art device illustrated in FIG. 3. The improved tubing organizer 10 includes a first strap 20, a second strap 30, a third strap which is folded over on itself to form a loop 40, a clip 50 and stainless steel eyelets 44, which are used with stainless steel washers 49.

First strap 20 has ends 22 and 26 and surface 24. Surface 24 is covered with fine, densely matted fibers 28. Surface 24 has three holes, 21, 23 and 25. Hole 21 is near end 22. Hole 23 is near end 26 and hole 25 is adjacent hole 23 in a direction away from end 26.

Second strap 30 has end 32, surface 34 and hole 31 near end 32. Surface 34 is covered with a plurality of generally rigid barbed extensions 38. First and second straps 20 and 30, respectively are made of a flexible, high temperature nylon. In the preferred embodiment they are Velcro ® strips.

First strap 20 and second strap 30 are joined at ends 22 and 32 by a stainless steel eyelet 44 which passes through holes 21 and 31 and washer 49. The washers 49 serve to broaden the contact area between eyelets 44 and straps 20, 30 and 40, thus preventing tearing. Surface 24 of first strap 20 opposes surface 34 of second strap 30. When first strap 20 and second strap 30 are pressed together, barbed extensions 38 adhere to the densely matted fibers 28. The strips, 20 and 30, can be easily pulled apart.

Loop 40 is made of a polytetrafluoroethylene, preferably Teflon ® and has holes 41, 43 and 45. Hole 41 is near end 42 of loop 40 and hole 43 is near end 46 of loop 40. Hole 45 is adjacent hole 43 in a direction away from the end 46. Hole 41 is in alignment with hole 43 when the third strap is folded over on itself to form loop 40. Alternatively, loop 40 may be a continuous loop rather than a strap folded to form a loop. Holes 41 and 43 are in alignment with hole 23 of first strap 20 when loop 40 is secured to surface 24 by a stainless steel eyelet 44 which passes through holes 23, 43 and 41 and washer 49. Loop 40 is also secured to surface 24 of first strap 20 by a stainless steel eyelet 44 which passes through holes 25 and 45 and another washer 49. This latter attachment prevents loop 40 from rotating around the stainless steel eyelet 44 which passes through holes 23, 43 and 41 and washer 49.

Clip 50 is made of stainless steel. Clip 50 is made of opposing jaws which are spring biased to facilitate the hold when fastened to an object. Any suitable known fastening device will serve the purpose. It is secured to loop 40 and first strap 20 by the stainless steel eyelet 44 which passes through holes 23, 43 and 41 and a washer 49. Loop 40 is disposed between clip 50 and surface 24 of first strap 20.

In use, the improved tube organizer 10 is capable of withstanding exposure to temperatures up to two hundred eighty degrees Fahrenheit. Loop 40 may be permanently attached to the tubing of heavily utilized equipment or to a length of tubing which will be used in the treatment of a particular patient during the course of hospitalization. Excess tubing or tubing from additional sources may be pressed between first and second straps 20 and 30, respectively, to hold the excess tubing in place. Clip 50 may then be fastened to the bed sheets or drapery to organize the tubing and prevent it from dangling freely or becoming entangled. When the tubing organizer 10 is no longer needed for a particular patient, it may be sterilized either by itself, after removing all tubes, or while still attached to its permanent hose via the Teflon ® loop 40. In both cases, the organizer 10 can be used to coil and organize other hoses being sterilized. Because of the materials chosen, the improved tubing organizer 10 has a long useful life through repeated sterilization cycles. Additionally, the loop 40 prevents loss of the organizer 10 in the event the Velcro ® strips are inadvertently pulled apart.

The prior art device 5 illustrated in FIG. 3 does not include a feature similar to loop 40. Accordingly, it can be lost or misplaced more easily than the improved organizer 10. Furthermore, device 5 uses stitching 7 to secure its first strap 4 to its second strap 6. Stitching 7 is also used to secure a Mylar ® strip 3 to first strap 4. A clip 9 is connected to the Mylar ® strip 3. The stitching 7 and Mylar ® strip 3 shorten the useful life of the prior art device 5 because they cannot withstand repeated exposure to the high temperatures of the sterilization process. The improved organizer 10 eliminates the Mylar ® strip 3 by securing the clip 50 directly to first strap 20. The stitching 7 is replaced by stainless steel eyelets 44 and washers 49, which are capable of withstanding higher temperatures and which will not wear or unravel as easily as will the threads of stitching 7. The improved device has a significantly longer lifespan through repeated sterilization cycles than does the prior art device. In studies comparing the performance of the two devices, the improved device had a lifespan ten times greater than the prior art device.

What is claimed is:

1. In an improved tubing organizing device of the type including a first strap having one surface of fine densely matted fibers, a second strap secured at one end to the first strap and having a surface which opposes the matted surface of the first strap, the opposing surface of the second strap having a plurality of generally rigid barbed extensions which adhere to the matted fibers of the surface of the first strap when the opposing surfaces are pressed together, and a clip attached to the first strap for fastening the device to an object, wherein the improvement comprises:

a third strap folded over on itself and secured to said first strap such that a closed loop is formed;

said loop being disposed between one end of said first strap and said clip, and said clip, loop and first strap being held together at a first point by a first eyelet;

said second strap being secured to the opposite end of said first strap by a second eyelet; and said loop being secured to said first strap at a second point by a third eyelet to maintain the alignment of said loop along said first strap;

wherein the materials which make up the device are capable of withstanding exposure to temperatures up to two hundred eighty degrees Fahrenheit.

2. The improvement of claim 1 wherein said eyelets are stainless steel eyelets.

3. The improvement of claim 1 wherein said third strap is made of Teflon ®.

4. The improvement as recited in claim 1 wherein said first and second straps are flexible high temperature nylon Velcro ® strips.

* * * * *